United States Patent [19]
Falkenberg et al.

[11] Patent Number: 5,449,617
[45] Date of Patent: Sep. 12, 1995

[54] CULTURE VESSEL FOR CELL CULTURES

[75] Inventors: Frank W. Falkenberg, Witten; Hans-Otto Nagels, Bovenden; Heinz-Gerhard Kohn, Dransfeld, all of Germany

[73] Assignee: Heraeus Sepatech GmbH, Osterode, Germany

[21] Appl. No.: 115,099

[22] Filed: Sep. 2, 1993

[30] Foreign Application Priority Data

Sep. 2, 1992 [DE] Germany .................. 42 29 325.1

[51] Int. Cl.$^6$ .................. C12M 1/02; C12M 3/00; C12M 1/06
[52] U.S. Cl. .................. 435/240.25; 435/240.1; 435/284; 435/287; 435/296; 435/312; 435/313; 435/316; 435/818
[58] Field of Search .............. 435/284, 285, 287, 296, 435/313, 813, 240.1, 240.23, 240.241, 818, 312, 316, 240.25

[56] References Cited

U.S. PATENT DOCUMENTS

| 4,717,668 | 1/1988 | Keilman et al. ............ 435/296 |
| 4,748,124 | 5/1988 | Vogler ............ 435/285 |
| 4,978,616 | 12/1990 | Dean et al. ............ 435/70.3 |
| 5,288,631 | 2/1994 | Baumgautner et al. ....... 435/240.242 |

FOREIGN PATENT DOCUMENTS

| 0180165 | 7/1987 | European Pat. Off. . |
| 3809163 | 9/1988 | Germany . |
| WO91/02555 | 3/1991 | WIPO . |

OTHER PUBLICATIONS

"The 'Glassmouse': A Rollerbottle-Like Apparatus for Culturing Hybridomas in Dialysis Bags", Thomas Hengelage et al., Ruhr-Universität Bochum Abteilung Für Medizinische Mikrobiologie Und Immunologie, Abstract 148, 1991 World Congress on Cell and Tissue Culture, Anaheim, Calif., Jun. 16–20, 1991.

Fisher Catalog p. 1631 Fisher Scientific, Pgh PA (1992).

Primary Examiner—William H. Beisner
Assistant Examiner—Jane Williams
Attorney, Agent, or Firm—Finnegan, Henderson, Farabow, Garrett & Dunner

[57] ABSTRACT

Culture vessels for cell cultures having at least one cell culture chamber containing a cell culture mixture that is separated by a dialysis membrane from a nutrient medium in a nutrient supply chamber. Nutrients are transported through the dialysis membrane into the cell culture chamber and metabolic products are transported out of the cell culture chamber into the nutrient supply chamber. To provide a culture vessel for generating cell cultures with a high cell density that is economical to manufacture and easy to handle and to reduce the danger of infections, a gas exchange membrane, that at least partly delimits the cell culture chamber and that is impermeable to liquids and to microorganisms that could contaminate the cell cultures is provided for feeding the gases required for cell culturing to the culture chamber and for discharging the gases generated during cell culturing.

21 Claims, 2 Drawing Sheets

CULTURE VESSEL FOR CELL CULTURES

BACKGROUND OF THE INVENTION

This invention relates to a culture vessel for cell cultures having at least one cell culture chamber containing a cell culture mixture, which is separated by a dialysis membrane from a nutrient chamber. Nutrients are transported from the nutrient chamber through the dialysis membrane into the cell culture chamber and metabolic products are transported out of the cell culture chamber into the nutrient chamber. A feed and discharge system is provided for the gases required and generated during cell culturing.

Culture vessels of this kind can be used, for example, for in vitro production of monoclonal antibodies. Monoclonal antibodies are currently produced for a number of purposes in diagnosis, treatment, and biomedical research, usually using hybridoma technology methods. "Hybridoma cells" is the term for immortalized hybrids of antibody-producing cells and myeloma cells. The antibodies produced by the hybridoma cells, which are characterized by high specificity, are referred to as "monoclonal" antibodies.

For in vitro antibody production, these hybridoma cells are cultured in certain liquid media whose composition corresponds as exactly as possible to that of blood. These media contain ingredients which include salts, sugar, vitamins, amino acids, and a buffer system based on sodium hydrogencarbonate ($NaHCO_3$). Usually the hybridoma cells are cultured in an incubator atmosphere with high atmospheric humidity and a $CO_2$ content that is at equilibrium with the $NaHCO_3$ present in the medium.

The monoclonal antibodies produced in this manner with conventional stationary in vitro methods, in the form of tissue culture supernantant, are very well suited for many purposes in basic biomedical research and in clinical diagnosis. However, for a number of applications in which pure monoclonal antibodies in high concentration are needed, the antibodies produced in stationary culture can only be used after laborious further processing. In the in vivo production form (ascites fluid), the monoclonal antibodies are already present in very high concentrations (up to 20 mg/ml) in the primary product. When monoclonal antibodies are produced with the usual stationary in vitro production methods, however, concentrations of only approximately 0.01 to 0.10 mg/ml are achieved.

To make possible the production of monoclonal antibodies at higher concentration and higher purity in vitro as well, a method and an apparatus in the form of a culture vessel similar to a roller bottle have been proposed, in which a "supply chamber" with nutrients for the cells being supplied, and a plurality of "production chambers" arranged therein in which cell growth occurs and in which the monoclonal antibodies are produced, are separated from one another by semipermeable dialysis membranes. Cells are supplied with nutrients from the "supply chamber" through the semipermeable dialysis membrane, while waste products and metabolic products are discharged, again through the dialysis membrane, from the "production chambers" into the "supply chamber." This apparatus has become known as the "Bochum glass mouse." This culture vessel for cell cultures is described, for example, in the paper entitled "The Glassmouse: A Rollerbottle-like Apparatus for Culturing Hybridomas in Dialysis Bags," presented by T. Henglage, F. Haardt, and F. W. Falkenberg at the 1991 World Congress on Cell and Tissue Culture in Anaheim, Calif. on Jun. 16–20, 1991. This culture vessel for cell cultures consists of a glass tube with an outside diameter of 120 mm, the ends of which are turned outward to form flanges. The length of the glass tube including the flanges is 320 mm. The ends of the glass are sealed with 15-mm thick polymethyl methacrylate (PMMA) disks. One of the PMMA disks has 5 through holes, one of them along the long axis of the vessel and sealed with a stopper that in turn has two smaller openings which are used to admit a $CO_2$/air mixture and to equalize pressure. For this purpose, a stainless steel tube with an inside diameter of 1 mm is passed through one of the two openings and extends to the opposite end of the glass tube and the $CO_2$/air mixture is fed through this and a sterile filter into the interior of the vessel. The four remaining holes in the PMMA disk surrounding the central hole are used to introduce dialysis bags, which project into the culture vessel and whose walls in each case consist of semipermeable dialysis membranes. The cell culture mixtures being cultured are placed in these dialysis bags, which act as production chambers, while the interior of the culture vessel additionally serves as the supply chamber for the cells, and is filled with nutrient medium to approximately 40% of its volume. The cells are supplied with nutrients from the supply chamber through the semipermeable dialysis membranes, while waste products and metabolic products are also discharged through the dialysis membrane. To allow the culture vessel to rotate about its long axis, it can be equipped with a sealed rotary leadthrough through which the supply line for the $CO_2$/air mixture passes.

This apparatus, in which the cells enclosed in the production chambers are surrounded by the semipermeable dialysis membranes, allows hybridoma cells to be cultured over longer periods and at high densities (more than $10^7$ cells/ml). The known culture vessel, however, is a relatively complex apparatus which is difficult to handle, the construction of which requires a certain skill that not every laboratory workshop can provide. In the known culture vessel, the gases necessary for cell metabolism and for creating physiological conditions are supplied by introducing into the supply chamber the gas mixture which constitutes the surrounding atmosphere; oxygen physically dissolves in the nutrient medium, and is transported from there through the dialysis membrane into the production chamber. Although the transport of oxygen from the supply chamber through the dialysis membrane into the cell culture chamber is not very efficient, it is sufficient for cell densities up to about $10^7$ cells/mi. Higher cell densities require an improvement in oxygen supply. Since at higher cell densities the cells' oxygen requirement is so high that the oxygen content in the cell culture chamber is exhausted in a few minutes, and the oxygen in the supply chamber is used up in less than one hour, additional oxygen must be delivered from the gas phase into the nutrient medium in the supply chamber. The weak point of the known culture vessel has proven to be the fact that continuous feeding of the $CO_2$/air mixture through the rotary leadthrough can cause infections of the cell cultures.

An object of the present invention therefore is to provide a culture vessel for the generation of cell cultures at high cell densities in which cell growth is not limited by an insufficient supply of oxygen to the cells, that can be produced economically and is easy to handle, and in which the danger of infections is reduced.

SUMMARY OF THE INVENTION

According to the invention this object is achieved, based on the culture vessel characterized above, by the fact that a gas exchange membrane that is impermeable to liquids and to microorganisms contaminating the cell cultures, which partly delimits a part of the cell culture chamber, is provided as a gas feed and discharge system. Because a membrane permeable to gases but impermeable to liquids and to microorganisms that could contaminate the cell cultures is provided as the gas feed and discharge system, infections of the cell culture or cultures brought in via the gas feed and discharge system can be almost avoided. Gas can be fed in and discharged by a gas exchange membrane without gas supply or discharge lines in the form of tubes or hoses. The culture vessel is therefore very easy to handle and easy to use, for example, as a roller bottle. Since the gases required for the gas supply are conveyed directly to the cell culture chamber, and gaseous metabolic products are discharged from the cell culture chamber directly through the gas exchange membrane, a more rapid gas exchange, and one that can be directly influenced by suitably adjusting the atmosphere surrounding the culture chamber, can be achieved. The gases necessary for cell respiration are primarily oxygen and carbon dioxide produced by the cell culture as the oxygen is consumed. By adjusting these gases in the atmosphere that surrounds the gas exchange membrane, their concentration in the cell culture chamber can be directly controlled. The total surface area, material, and thickness of the gas exchange membrane must be selected so as to guarantee an oxygen supply that meets oxygen requirements at the desired high cell densities. Suitable gas exchange membrane geometries and gas permeabilities can be determined with a few experiments.

Suitable cell cultures include, for example, hybridoma cells, tumor cells, or transfacted tumor cells.

BRIEF DESCRIPTION OF THE DRAWINGS

Exemplary embodiments of the invention are shown in the drawings and will be explained in more detail below. Of the drawings in schematic form.

DETAILED DESCRIPTION OF THE INVENTION

Figure 1:
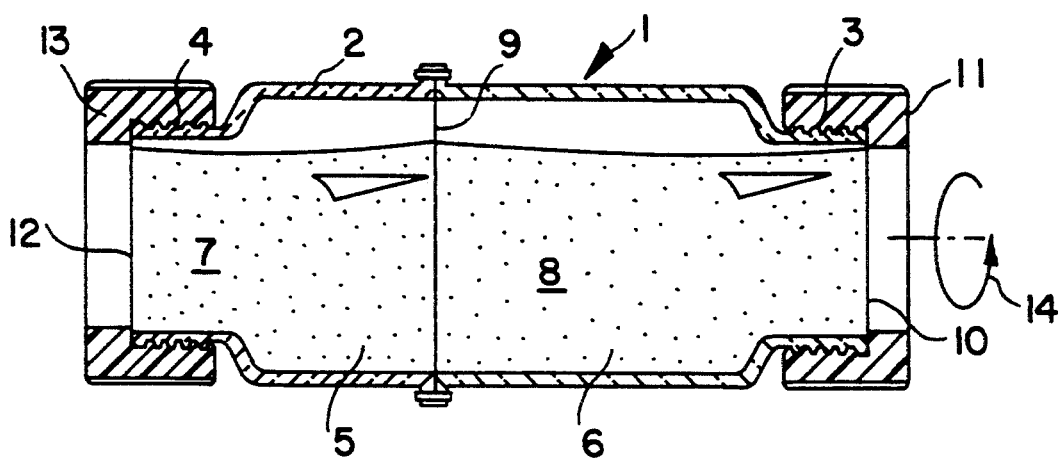
FIG. 1 shows a culture vessel similar to a roller bottle for cell cultures, with one cell culture chamber and one supply chamber, in lengthwise cross section.

In FIGS. 1 to 6, the culture vessel in its entirety is assigned the reference number 1. The culture vessel 1 is similar to a roller bottle, meaning that it is designed substantially in the shape of a hollow cylinder. Its peripheral surface consists of a glass tube 2 open at both ends, provided in the region of each end with external threads 3, 4. The culture vessel 1 has two chambers that can be detached from one another, specifically a cell culture chamber 5 and a supply chamber 6. The cell culture chamber 5 contains the cell culture mixture 7 being cultured, while the supply chamber 6 contains a nutrient medium 8. The two chambers are separated from one another vertically by a dialysis membrane 9, through which nutrients are transported from the supply chamber 6 into the cell culture chamber 5, and, conversely, metabolic products are transported out from the cell culture chamber 5 into the supply chamber 6. The end of the glass tube 2 associated with the supply chamber is sealed with a gas-permeable PTFE disk 10 that is 0.3 mm thick that is pressed in a liquid-tight manner against the glass tube 2 by means of an annular twist-on ring or cap 11 engaging the external threads 3 of the glass tube 2. To top up or replace the nutrient medium 8, the twist-on ring 11 is opened and the PTFE disk 10 is removed. The end of the glass tube 2 associated with the cell culture chamber 5 is sealed with a silicone membrane 12 having a thickness of about 0.5 mm, which serves as a gas exchange membrane. The silicone membrane 12, which is permeable to oxygen and carbon dioxide gas, covers an area of about 10 cm$^2$. It is attached to the glass tube 2 in a liquid- and bacteria-tight manner by means of a screw-on ring 13. The cell culture chamber 5 can accommodate a volume of about 60 ml; the total volume of the supply chamber 3 is approximately 300 ml.

The culture vessel 1 can be rotated about its long axis, for example, on a conventional roller rotation apparatus (not shown) as indicated by the directional arrow 14. Concurrently with its rotation, a slow, cyclical tumbling movement can be imparted to the culture vessel 1, in which the ends of the culture vessel 1 continuously move up and down relative to one another in the manner of a seesaw. This causes mixing of the liquid nutrient medium 8 and of the cell culture mixture 7, ensuring that by means of the respective membranes 12, 9 the cell culture mixture 7 is steadily supplied with the gases necessary for cell respiration and with nutrients from the nutrient medium 8, respectively, and metabolic products are continuously transported out of the cell culture 7 mixture into the nutrient medium 8 or into the incubator atmosphere.

The gas exchange necessary to supply gases to and remove gases from the cell culture mixture 7 occurs principally via the silicone membrane 12. The silicone membrane 12 is selected so that neither nutrients nor metabolic products of the cell culture mixture 7 can pass through it or clog it. This guarantees free and unhindered gas exchange between the cell culture chamber 5 and the incubator atmosphere surrounding it. The cell culture is also indirectly supplied with oxygen brought into the supply chamber through the PTFE disk 10. In an exemplary embodiment in which the volume of the cell culture mixture 7 is approximately 35 ml, a yield of more than 10$^7$ cells per milliliter of cell culture mixture is expected. The permeability of the silicone membrane 12 to oxygen is selected to be to approximately 3 mg/h. According to the invention, for example, the oxygen necessary for cell multiplication passes from outside, through the silicone membrane 12, directly into the cell culture 7 itself, and also into the atmosphere above the cell culture 7, from whence it is then also incorporated transferred into the cell culture 7. This type of oxygen input makes the oxygen supply to the cell culture 7 particularly effective, fast, and easily influenced from the outside. The concentration of the carbon dioxide gas that forms as a metabolic product, which is in equilibrium with the $NaHCO_3$ present in the medium of the cell culture chamber 5, can also be discharged to the outside quickly and relatively precisely via the silicone membrane 12, due to the direct gas exchange between the cell culture chamber 5 and the incubator atmosphere surrounding it.

The primary task of the gas exchange membrane is to ensure the gas exchange necessary for cell culturing. In contrast to the dialysis membrane in the known culture vessel, which must supply not only gases but also nongaseous nutrients, it can therefore be optimized for this task. Moreover, being on the side facing away from the nutrient supply chamber, the gas exchange membrane can be exposed directly to the gas, in other words without any interfering intermediate layers or surface films. Pressure changes or changes in gas composition are transferred directly to the gas exchange membrane.

Materials that have a permeability coefficient for oxygen of at least $1 \times 10^{19}$ $m^2 \times Pa$, preferably at least $5 \times 10^{19}$ $m^2/s \times Pa$, have proven suitable for the gas exchange membrane. Silicone and microporous hydrophobic or hydrophobized material have proven to be particularly good materials for the gas exchange membrane. To guarantee sufficient oxygen supply, the thinnest possible gas exchange membranes are preferred; membranes with a thickness between 0.1 mm and 1 mm have proven successful. A silicone membrane and can be manufactured economically in any desired shape by injection molding. Silicone is available commercially in many thicknesses, shapes, and specific gas permeabilities. It has high tear resistance and good chemical resistance to the media ordinarily used in cell culturing, and is therefore also especially easy to handle. The easy sterilizability of a silicone gas exchange membrane is also especially advantageous; in particular, it can be sterilized in an autoclave very effectively and with no substantial changes in shape. It can therefore also be used several times. Microporous, hydrophobic polytetrafluoroethylene (PTFE) has also proven advantageous as a material for the gas exchange membrane. Its hydrophobic nature ensures that the gas exchange membrane is impermeable to aqueous media. For a given gas permeability, the required geometry of the gas exchange membrane depends on the gas requirement resulting for cell respiration, and on the partial pressures of the gases involved in cell respiration, especially on the oxygen partial pressure acting on it from outside. With an external pressure of 1 atm and an incubator atmosphere with an oxygen partial pressure corresponding approximately to that of air, gas exchange membranes with a surface area of at least 5 $cm^2$ have proven suitable for cell cultures of 35 ml and $10^7$ cells per milliliter of cell cultures mixture.

The reference numbers used in FIGS. 2 to 6 refer to components of the culture vessel 1 that are identical or equivalent to those described in FIG. 1. In the embodiment of the culture vessel 1 depicted in FIG. 2, a cell culture chamber 5 is provided that is separated by a dialysis membrane 9 from a supply unit 15 made of a porous carrier substance and containing a gel-like nutrient medium 8. Since in this case the dialysis membrane 9 is in contact with a substantially solid supply unit 15 and is thus stabilized by it, it can be made very thin, namely 0.01 mm. Exchanges of nutrients and metabolic products therefore take place in a very quick and unhindered manner. The gases necessary for cell respiration are once again delivered to the cell culture 7 through a silicone membrane 12 approximately 0.5 mm thick. Conversely and simultaneously, the volume of $CO_2$ gas produced when oxygen is utilized by the cell culture 7 is discharged through the silicone membrane 12.

Figure 2:
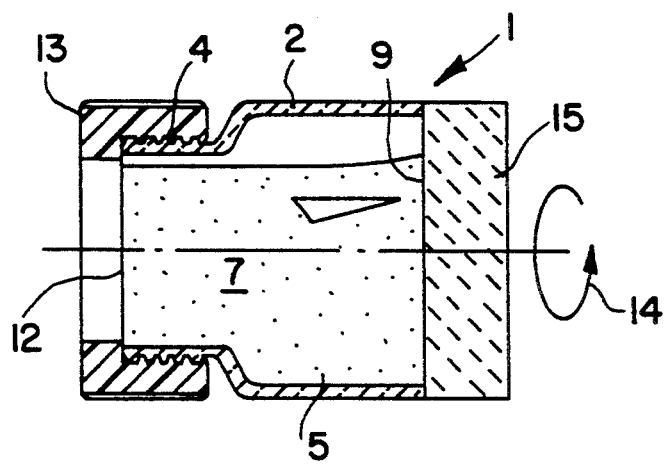
FIG. 2 shows a culture vessel similar to a roller bottle, with one cell culture chamber and one supply unit, in lengthwise cross section.

This culture vessel in which the cell culture chamber has two approximately opposite surfaces, one surface forming the dialysis membrane, is of particularly simple design. As shown in FIG. 2, the surface of one end can consist of the dialysis membrane 9, next to which is supply unit 15 containing the nutrient medium and the surface of the other end can, for example, constitute the gas exchange membrane 12. If the culture vessel is used as a roller bottle, the peripheral surface can serve as the rolling contact surface.

In this embodiment of the culture vessel, it is especially advantageous if the membranes are designed as simple films or flat membranes, which are simple to manufacture and easy to clean and sterilize. Furthermore, the fact that the membranes delimit the cell culture chamber vertically makes them easier to handle independently of the other parts of the culture vessel, and allows a modular design for the culture vessel.

Figures 3, 4:
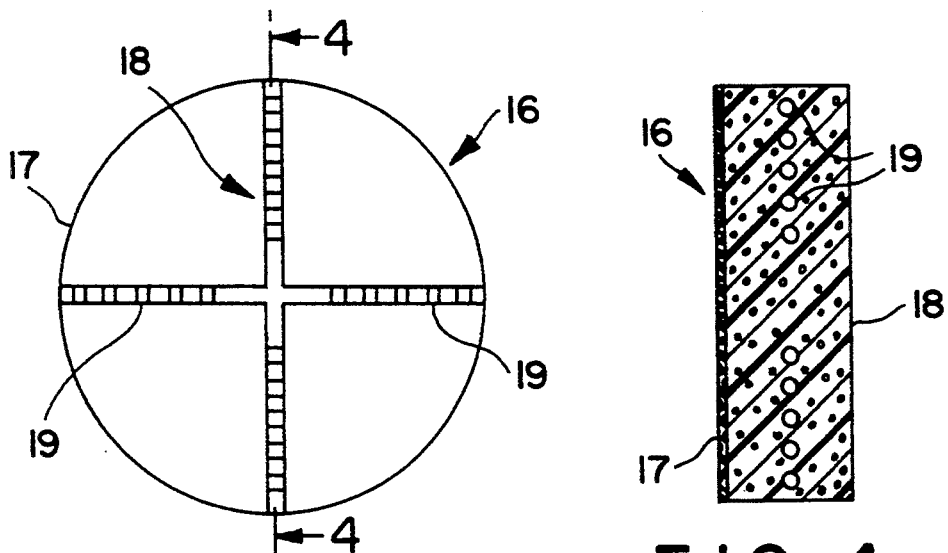
FIG. 3 is a top view of a gas exchange membrane equipped with mixing elements.
FIG. 4 is a sectional view taken along the line 4—4 of FIG. 3.

The gas exchange membrane 16 depicted in FIG. 3 consists of a silicone membrane 17, approximately 0.2 mm thick, that is equipped with mixing elements designed is of the culture vessel, and allows a modular design for the culture vessel.

The gas exchange membrane 16 depicted in FIG. 3 consists of a silicone membrane 17, approximately 0.2 mm thick, that is equipped with mixing elements designed in the form of intersecting silicone webs 18 approximately 2 mm high. The silicone membrane 17 is located in the culture vessel 1 in such a manner that the silicone webs 18 project inwardly into the medium being mixed (cell culture and/or nutrient medium). The silicone webs 18 are provided with passages 19 that are distributed approximately evenly over the length of the webs 18. These passages 19 contribute to better mixing of the medium. It is evident from the side view, depicted in FIG. 4, of a section through the membrane taken along the line 4—4 in FIG. 3, that the round passages 19 are distributed evenly over the length of the webs 18 and run perpendicular to the axial direction, with a diameter of about 1 mm. Advantageously, the height of the webs 18 is selected so that they project from the membrane 17 as far as the opposite dialysis membrane (not shown), so that the cell culture chamber (also not shown) will be divided into a plurality of individual chambers in which the cell cultures are mixed principally by the air bubbles generated by the passages 19 as the membranes 17 rotate.

Particularly high cell densities can be achieved with culture vessels in which these mixing elements are utilized in the cell culture chamber. The mixing elements produce good mixing of the cell culture, and therefore ensure a steady supply of nutrients to the entire cell culture. A culture vessel in which the mixing elements consist of flat web members 18 that are attached to the dialysis membrane and/or the gas exchange membrane has proven to be particularly easy to handle and economical to manufacture. Particularly effective and reproducible mixing of the cell culture occurs in a culture vessel in which the membrane and the flat web members are designed as a single unit and are made of the same material. The embodiment of the gas exchange membrane shown in which the mixing elements are paddle-like webs projecting from the membrane and provided with passages distributed over their length and running perpendicular to the long axis has proven especially advantageous. When the webs move in a liquid medium and, for example, rotate about an axis extending perpendicular to the long axis of the webs, the passages generate air bubbles that contribute to excellent turbulence in the medium being mixed. As noted, preferably the webs extend from one membrane to an opposite membrane, extending parallel to the first.

A culture vessel in which the gas exchange membrane has thickened regions has also proven advantageous. These regions can be used, for example, to take samples from the cell culture or to inoculate the cell culture or cultures. Because these regions are thickened, the opening caused by insertion of the sampling or inoculation needle automatically seals itself after the needle is removed. It is also possible to pierce the same insertion opening several times at the same point.

Figure 5:
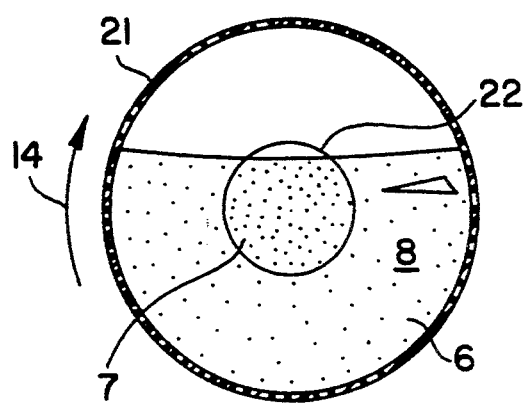
FIG. 5 is a cross section through a culture vessel similar to a roller bottle, with one supply chamber and one cell culture chamber arranged inside thereof.

The culture vessel 1 shown in FIG. 5 consists substantially of a silicone tube 21 which forms the supply chamber 6 and, in a horizontal orientation, is filled to somewhat more than half its height with nutrient medium 8. Extending inside the silicone tube 21 and coaxially with it is a dialysis bag 22 partly filled with the cell culture 7, which extends from one end of the silicone tube 21 to the opposite end. The ends of both the silicone tube 21 and the dialysis bag 22 terminate flush with one another and are each sealed off from the outside by a shared silicone membrane (not shown in the Figure). Gas exchange occurs both between the supply chamber 6, and directly with the cell culture 7, via the silicone tube 21 and the silicone membrane. The cell culture 7 is supplied with nongaseous nutrients via the wall of the dialysis bag 22, which is designed as a semipermeable membrane.

In this embodiment of the culture vessel, the cell culture chamber is delimited on all sides by the dialysis membrane and gas exchange membrane so that the surface areas of the dialysis membrane and the gas exchange membrane are made sufficiently large to ensure that the cell culture is supplied with nutrients and with the gases needed for cell respiration and to maintain physiological conditions, and to ensure that metabolic products are transported out. High cell densities can be achieved if the cell culture or cultures are supplied with a sufficient quantity of nutrients and with the gases required for metabolism, provided the resulting metabolic products are at the same time continuously transported out. Particularly rapid gas exchange and particularly high cell densities can be achieved with a culture vessel whose entire outer wall, except for any necessary support elements, is designed as a membrane.

Figure 6:
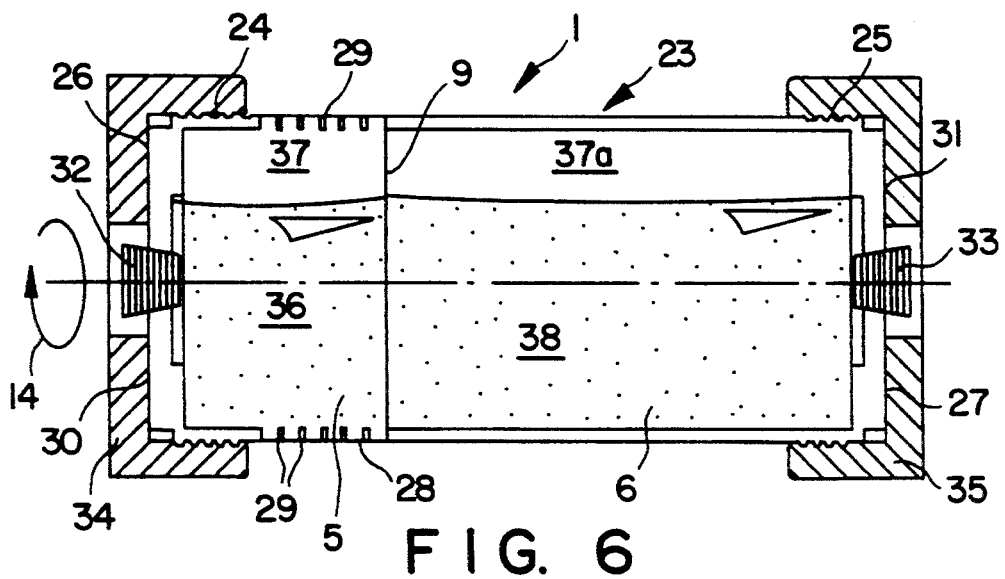
FIG. 6 shows a culture vessel similar to a roller bottle, with one cell culture chamber and one supply chamber that is substantially delimited by membranes, in lengthwise cross section.

In the embodiment of the culture vessel 1 according to the invention shown in FIG. 6, both the cell culture chamber 5 and the supply chamber 6 are arranged inside a silicone tube 23. These are separated from one another by a flat, semipermeable dialysis membrane 9. The silicone tube 23 is provided in its end regions with external threads 24, 25 and with flanges 26, 27 pointing inward.

The wall thickness of the silicone tube 23 is approximately 3 mm. The portion of the silicone tube 23 surrounding the cell culture chamber 5 has evenly distributed openings that occupy approximately two thirds of the peripheral surface of this part of the silicone tube 23, and are covered on the outside with a silicone membrane 28 0.38 mm thick. The interconnected webs 29 remaining in this portion of the peripheral surface of the silicone tube 23 project from the silicone membrane 28 into the interior of the cell culture chamber 5, and form a cohesive grid. They thus impart to the cell culture chamber 5 sufficient mechanical stability for the stresses that occur during culturing. The culture vessel 1 has a length of approximately 15 cm, an outside diameter of approximately 5 cm, and can contain a total volume of approximately 300 ml, of which approximately 60 ml is accounted for by the cell culture chamber 5. The total peripheral surface area of the silicone tube 23 is approximately 240 $cm^2$. The ends of the silicone tube 23 are each sealed with an annular disk 30, 31 with a center hole, made of a stable plastic. The annular disks 30, 31, the center holes of each of which can be sealed with a rubber stopper 32, 33, are pressed in a fluid-tight manner against the flanges 26, 27 of the silicone tube 23 by means of annular screw caps 34, 35 that engage with the external threads 25, 26 on culture vessel 1. Rubber stoppers 32, 33 are accessible through openings in the screw caps 34, 35. The culture vessel 1 can rotate about its long axis, as indicated by the directional arrow 14.

Especially with regard to the geometrical stability of the culture vessel and therefore the reproducibility of the results obtained with it, it is advantageous to provide the gas exchange membrane and/or the dialysis membrane with a support element which mechanically stabilizes the membrane. Such support elements stabilize the shape and geometrical arrangement of the individual parts of the culture vessel with respect to one another under the mechanical stresses that act on the outer walls of the culture vessel when the culture vessel is used as a roller bottle and are preferred in particular for thin-walled membranes and those that span large areas.

The above described culture vessel in which the gas exchange membrane and/or the dialysis membrane contains a mechanically stable support framework which is covered by a material forming the membrane has proven especially successful. As shown, the support framework is preferably designed in the form of a network or a grid. A metal or a mechanically and chemically stable plastic can be used as the support material, but a support framework made of the same material as the membrane covering it is preferred, in which case mechanical stability can be achieved by the fact that the support framework has thicker walls than the membrane itself. Advantageously, thickened regions of the support framework project from the surface of the membrane into the interior of the culture vessel. The resulting flat members serve, when the culture vessel moves, as mixing elements for the cell culture and/or for the nutrient medium. The membrane covering the support framework can be produced, for example, by saturating the support framework with a material or with a plurality of different materials, especially plastics or suitable precursor products that form plastics, which, for example, are cured after saturation on the support framework. Different membrane materials, adapted to the respective requirements, can be used for the gas exchange membrane and the dialysis membrane.

In use, the cell culture chamber 5 is filled with approximately 35 ml of cell culture mixture 36, and the cell culture chamber 5 is then sealed with rubber stopper 32. As a result, an air space 37 with a volume of about 25 ml is created in the cell culture chamber 5. At the same time, the supply chamber 6 is filled to about half its height (when oriented horizontally) with nutrient medium 38 for the cell culture mixture 36. Cell culturing occurs in a medium that depends on a NaHCO$_3$ buffer. To maintain the buffer system, the culture vessel is placed in an incubator (not shown in the Figure) having a predetermined CO$_2$ and O$_2$ atmosphere, high atmospheric humidity, and defined temperature. As the culture vessel 1 rotates in the incubator, the dialysis membrane 9 is bathed on all sides with the nutrient medium 38. As a result, nutrients are transported from the supply chamber 6 into the cell culture chamber 5 containing the cell culture mixture 36 and, at the same time, metabolic products are transported out of it into the supply chamber 6. The oxygen present in the incubator atmosphere passes through the thin silicone membrane 28, which has sufficient permeability to oxygen to meet the oxygen requirement of the cell culture 36 (at least 0.01 mg/h per 10$^7$ cells), directly into both the cell culture 36 and the air space 37 located above it. In addition, smaller amounts of oxygen also enter the cell culture 36 through the dialysis membrane 9 from the supply chamber 6. The carbon dioxide gas produced as the oxygen is consumed is also removed from the culture chamber 5 primarily though the silicone membrane 28. The permeability of the silicone membrane 28 to carbon dioxide gas is substantially greater than its permeability to oxygen, so that excess pressure cannot build up inside the cell culture chamber 5. The silicone film 28 is, on the other hand, impermeable to liquids and to microorganisms that might contaminate the cell culture 36, such as bacteria, fungi, or spores. During culturing, samples can be removed, the cell culture 36 can be inoculated, or the nutrient medium 38 can be checked or replaced, via the respective rubber stoppers 32, 33.

To obtain good mixing of both the cell culture 36 and the nutrient medium 38, the culture vessel 1 is rotated about its long axis at a rotation speed of about 34 rpm. Superimposed on this rotation direction 14 is a slow, cyclical tumbling movement of the culture vessel 1, in which the ends of the silicone tube 23 move continuously up and down in a seesaw manner. As a result of their buoyancy in the cell culture 36, the air bubble in air space 37 therefore also moves up and down inside the cell culture chamber 5, thus promoting mixing of the cell culture 36, and supplying it steadily with nutrients (especially oxygen), in a particularly effective manner.

Because the nutrient medium 38 is made available in a separate supply chamber adjacent to the cell culture chamber, it is possible to renew or check the nutrient medium. As a result, the dialysis membrane is constantly in contact with nutrient medium, and the cell culture or cultures are constantly being supplied. A culture vessel of this kind is especially easy to handle, particularly in terms of replacing and adding nutrient medium or taking samples, if the supply chamber is provided with a filler opening through which the liquid nutrient medium can be placed in the nutrient chamber or withdrawn from it.

Figure 7:
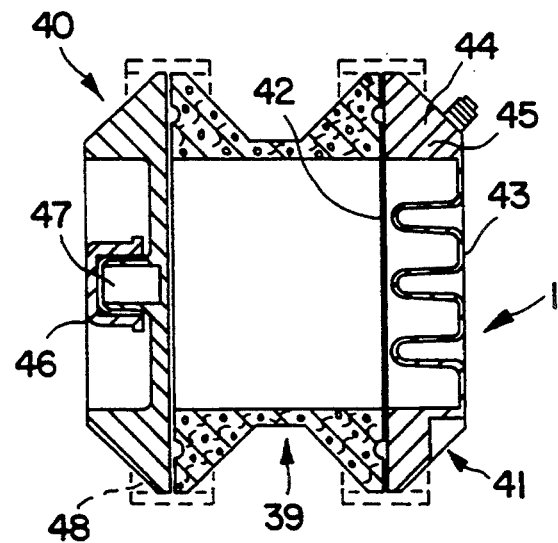
FIG. 7 shows a culture vessel according to the invention constructed in modular fashion, with a folded gas supply membrane, in cross section.

FIG. 7 depicts a culture vessel 1 according to the invention at a scale of 1:1. It is composed, in modular fashion, of a sleevelike center part 39 made of polysulfone and containing the nutrient medium. A cover plate 40 seals one end of the center part 39 in a liquid-tight manner and a cell culture chamber 41 is arranged at the opposite end of the center part 39 and contains the cell culture mixture. The center part 39, containing the nutrient medium for the cell culture, is separated from the cell culture chamber 41 by a semipermeable dialysis membrane 42. The dialysis membrane 42 is associated with the cell culture chamber 41, the remainder of which is made of silicone. The side of the cell culture chamber 41 opposite the dialysis membrane 42 is designed as a thin-walled molded silicone element 43 folded in the manner of a bellows, while the side wall consists of a thick-walled silicone ring 44 that mechanically stabilizes the cell culture chamber 41. A sealable filler opening 45 extends through the wall of the silicone ring 44 into the cell culture chamber 41. The volume of the cell culture chamber 41 is about 35 ml. The molded silicone element 43 has a wall thickness of 0.2 mm, and is sufficiently permeable to oxygen that no oxygen shortage occurs even at cell densities greater than 10$^7$ cells/ml. In order to increase its surface area and therefore further increase the volume of oxygen diffusing through it, the molded silicone element 43 is designed in the form of a bellows. The cover plate 40 has an opening 47 that can be closed with a cap 46, through which the nutrient medium can be added. The individual modules 39, 40, 41 of the culture vessel 1 are held together by clamps 48 that engage at their periphery.

A culture vessel in which the dialysis membrane and the gas exchange membrane are made of the same material is especially easy to manufacture. The essential parts of a culture vessel of this kind can, for example, be manufactured as simple molded or injection-molded parts. Different properties, for example, different permeabilities for the dialysis membrane and the gas exchange membrane, can be produced by adding fillers to one type of membrane, or different fillers to the two types of membranes. The fillers can be incorporated into the respective membrane regions, for example, by saturating the respective membrane regions with suitable solutions that contain the fillers in the form of a precursor product. If necessary, the fillers can be consolidated in the membrane after saturation.

Moreover, a culture vessel in which the gas exchange membrane is folded is advantageous, especially with regard to a high cell density within the cell culture. This increases the total surface area of the gas exchange membrane for a given area covered by the gas change membrane, thus improving gas exchange and in particular the supply of oxygen to the cells. With hollow cylindrical culture vessels, for example, the peripheral surface can be designed in the form of a bellows, which are easy to manufacture.

The culture vessel according to the invention is particularly easy to handle. It can produce high-purity cell cultures with cell densities of more than 10$^7$ cells/ml, and, in the case of hybridoma cells, concentrations of monoclonal antibodies that are at least ten times greater than the concentrations attainable with standard stationary cultures.

We claim:
1. A culture vessel for cell culture comprising an elongated, generally cylindrical housing defining at lease one cell culture chamber adapted to contain a cell culture mixture, one or more mixing elements fixed relative to said housing and extending into said cell culture chamber, at least one nutrient retaining means adapted to contain a nutrient medium for said cell culture, a dialysis membrane separating the cell culture chamber from the nutrient retaining means, wherein nutrients can be transported from the nutrient retaining means through the dialysis membrane into the cell culture chamber to cultivate cells and metabolic products produced in the cell culture chamber can be transported from the cell culture chamber through the dialysis membrane to the nutrient retaining means, and a gas exchange membrane that is impermeable to liquids and to microorganisms capable of contaminating the cell culture mixture forming at least partially a wall of said cell culture chamber through which gases required for cell culturing can be fed and gases generated during cell culturing can be discharged, wherein said one or more mixing elements in the cell culture chamber are attached to the gas exchange membrane.

2. The culture vessel of claim 1, wherein the gas exchange membrane is of a microporous hydrophobic material.

3. The culture vessel of claim 2, wherein the gas exchange membrane is of silicone.

4. The culture vessel of claim 3, wherein the gas exchange membrane has a thickness of from 0.1 mm to 1.0 mm.

5. The culture vessel of claim 1, wherein the gas exchange membrane has a surface area of at least 5 $cm^2$.

6. The culture vessel of claim 1, wherein said one or more mixing elements comprise a plurality of flat web-like paddles.

7. The culture vessel of claim 6, wherein the flat web-like paddles are formed of the same material as the gas exchange membrane.

8. The culture vessel of claim 7, wherein the flat web-like paddles and the gas exchange membrane are configured as a single unit.

9. The culture vessel of claim 1, wherein means are provided on the gas exchange membrane for inserting a needle into said cell culture chamber, said means including locally thickened portions of said gas exchange membrane.

10. The culture vessel of claim 1, wherein the housing and the gas exchange membrane are formed of the same material.

11. The culture vessel of claim 1, wherein the gas exchange membrane lies adjacent to and is supported by a support element.

12. The culture vessel of claim 11, wherein the gas exchange membrane covers a support framework.

13. The culture vessel of claim 1, wherein the nutrient retaining means for the nutrient medium is at least one nutrient supply chamber for holding the nutrient medium that is separated from the cell culture chamber by the dialysis membrane.

14. The culture vessel of claim 13, wherein an opening is provided in an outer wall of the supply chamber for supplying nutrient medium to said supply chamber.

15. The culture vessel of claim 13, in which the at least one supply chamber and the at least one cell culture chamber are individual elements.

16. The culture vessel of claim 1, wherein the cell culture chamber has two approximately oppositely located delimiting surfaces, one of which is formed by the dialysis membrane and the other of which by the gas exchange membrane.

17. The culture vessel of claim 1, wherein the cell culture chamber is delimited on all sides by membranes, of which a portion consists of the dialysis membrane and another portion consists of the gas exchange membrane, the surface areas of the dialysis membrane and the gas exchange membrane being large enough so that the cell culture is supplied with nutrients and with the gases needed for cell cultivation, and that metabolic products produced are transported out of the cell culture chamber.

18. The culture vessel as in claim 1, wherein said housing has a roller bottle configuration, and an outer peripheral surface comprising a rolling contact surface.

19. A method of culturing cells in a culture vessel of the type having a cell culture chamber and a nutrient retaining chamber separated by a dialysis membrane, and a gas exchange membrane forming at least part of the culture chamber wall, the method comprising the steps of:

placing a cell culture mixture in the cell culture chamber of the culture vessel;

placing nutrient medium in the nutrient retaining chamber of the culture vessel;

transporting nutrients across the dialysis membrane from the nutrient retaining chamber to the cell culture chamber to cultivate cells;

transporting metabolic products produced in the cell culture chamber across the dialysis membrane to the nutrient retaining chamber;

feeding gases required for cell culturing into the cell culture chamber across the gas exchange membrane;

discharging gases generated during the cell culturing through the gas exchange membrane; and moving the culture medium relative to the nutrient medium, wherein the culture vessel used includes one or more mixing elements fixed to the gas exchange membrane and extending into the cell culture chamber, and wherein the moving step includes rotating the culture vessel including the gas exchange membrane and one or more mixing elements fixed thereto to provide mixing of the culture medium.

20. The method of claim 18, wherein a step of cyclical tumbling the culture vessel about an axis transverse to the axis of rotation is carried out simultaneously with said rotating step.

21. The method as in claim 20, wherein the cell culture mixture placing step includes only partially filling the respective chamber to promote mixing.

* * * * *

UNITED STATES PATENT AND TRADEMARK OFFICE
CERTIFICATE OF CORRECTION

PATENT NO. : 5,449,617
DATED : September 12, 1995
INVENTOR(S) : Falkenberg et al.

It is certified that error appears in the above-indentified patent and that said Letters Patent is hereby corrected as shown below:

Claim 20, col. 12, line 52, change "claim 18" to --claim 19-.

Signed and Sealed this

Twenty-first Day of November, 1995

Attest:

BRUCE LEHMAN

Attesting Officer

Commissioner of Patents and Trademarks